US00PP18842P2

(12) United States Plant Patent
Whetman

(10) Patent No.: US PP18,842 P2
(45) Date of Patent: May 27, 2008

(54) *DIANTHUS* PLANT NAMED 'WP05 ENID'

(50) Latin Name: *Dianthus×hybrida*
Varietal Denomination: WP05 Enid

(76) Inventor: John Whetman, Deer Park Farm, Chudleigh, Devon (GB), TQ13 ONH ( * ) Notice: Subject to any disclaimer, the term of this patent is extended or adjusted under 35 U.S.C. 154(b) by 94 days.

(21) Appl. No.: 11/523,297

(22) Filed: Sep. 18, 2006

(51) Int. Cl.
*A01H 5/00* (2006.01)

(52) U.S. Cl. ..... Plt./273

(58) Field of Classification Search ..... Plt./273, Plt./277
See application file for complete search history.

*Primary Examiner*—Kent L. Bell

(57) ABSTRACT

A new cultivar of *Dianthus* plant named 'WP05 ENID' that is characterized by compact mounding habit, gray-green foliage and mildly fragrant pink flowers with large red-purple markings. In combination these traits set 'WP05 ENID' apart from all other existing varieties of *Dianthus* known to the inventor.

2 Drawing Sheets

Genus: *Dianthus.*
Species: ×*hybrida.*
Denomination: 'WP05 ENID'.

BACKGROUND OF THE INVENTION

The present invention relates to a new and distinct cultivar of *Dianthus,* or garden pink, that is grown for use as an ornamental landscape and container plant. It is known botanically as *Dianthus×hybrida* and will be referred to hereinafter by the cultivar name 'WP05 ENID'. It is one of two applications by the inventor of two co-pending cultivars of *Dianthus.* The other is titled Dianthus Plant Named 'WP05 YVES' U.S. Plant patent application Ser. No. 11/523,431.

'WP05 ENID' is the product of a breeding program started by the inventor in 1985 in a cultivated area of Houndspool, Dawlish, Devon, United Kingdom. The primary focus of the breeding program is to produce new cultivars of garden pinks that exhibit unique characteristics of flower color and form, and which, preferably, are highly and pleasantly fragrant. In addition, new varieties are selected for being well-proportioned in respect of ratio of overall height (including flower canopy) to overall width.

Ordinarily, the inventor carries out controlled crosses, with known parents, and selected new varieties for sets of similar characteristics in order to make whole sets of series. 'WP05 ENID' is a chance hybrid plant that was selected in 2003 as a single seedling from a large group (which the inventor designated as Family 9722) of open-pollinated seedlings which itself had resulted from open-pollination of a group of unnamed and unreleased plants of *Dianthus* from the inventor's large collection of *Dianthus.* Thus, on this occasion, the inventor is unable to identify either the male or the female parent, or to draw comparisons between 'WP05 ENID' and either parent.

'WP05 ENID' was selected for its distinguishing combination of compact well-proportioned habit, floriferous blooming, perfume fragrance and double bi-colored flowers. The closest cultivar known to the inventor is *Dianthus* Plant names 'DEVON YOLANDE' (U.S. Plant Pat. No. 16,029). 'WP05 ENID' is distinguished from 'DEVON YOLANDE' by having a large red-purple center area in each flower whereas 'DEVON YOLANDE' has a small red-purple center area in each flower.

Asexual reproduction of the new cultivar was first accomplished by the inventor in 2003, in a cultivated area of Houndspool, United Kingdom. The method of asexual propagation used was stem cuttings. Since that time the characteristics of the new cultivar have been determined stable and are reproduced true to type in successive generations of vegetative propagation.

SUMMARY OF THE INVENTION

The following traits have been repeatedly observed and represent the characteristics of the new *Dianthus* cultivar 'WP05 ENID'. These traits in combination distinguish this cultivar from all other commercial varieties known to the inventor. 'WP05 ENID' has not been tested under all possible conditions and phenotypic differences may be observed with variations in environmental, climatic and cultural conditions without however any difference in genotype.

1. *Dianthus* 'WP05 ENID' exhibits a compact mounding growth habit.
2. *Dianthus* 'WP05 ENID' exhibits gray-green foliage.
3. *Dianthus* 'WP05 ENID' exhibits fragrant pink flowers with red-purple markings.
4. *Dianthus* 'WP05 ENID' is 20–25 cm in overall height, including flower canopy, and 25–30 cm in width in a 1.5-litre container.
5. *Dianthus* 'WP05 ENID' is an evergreen perennial ornamental.
6. *Dianthus* 'WP05 ENID' blooms from May to October.
7. *Dianthus* 'WP05 ENID' is hardy to minus 15° Centigrade.

BRIEF DESCRIPTION OF THE DRAWINGS

The accompanying color drawings illustrate the overall appearance of the new *Dianthus* variety 'WP05 ENID' showing colors as true as it is reasonably possible to obtain in colored reproductions of this type. Colors in the drawings may differ from the color values cited in the detailed botanical description, which accurately describe the actual colors of the new variety 'WP05 ENID'.

The drawing labeled as FIG. 1 illustrates the entire plant in flower.

Figure 1:
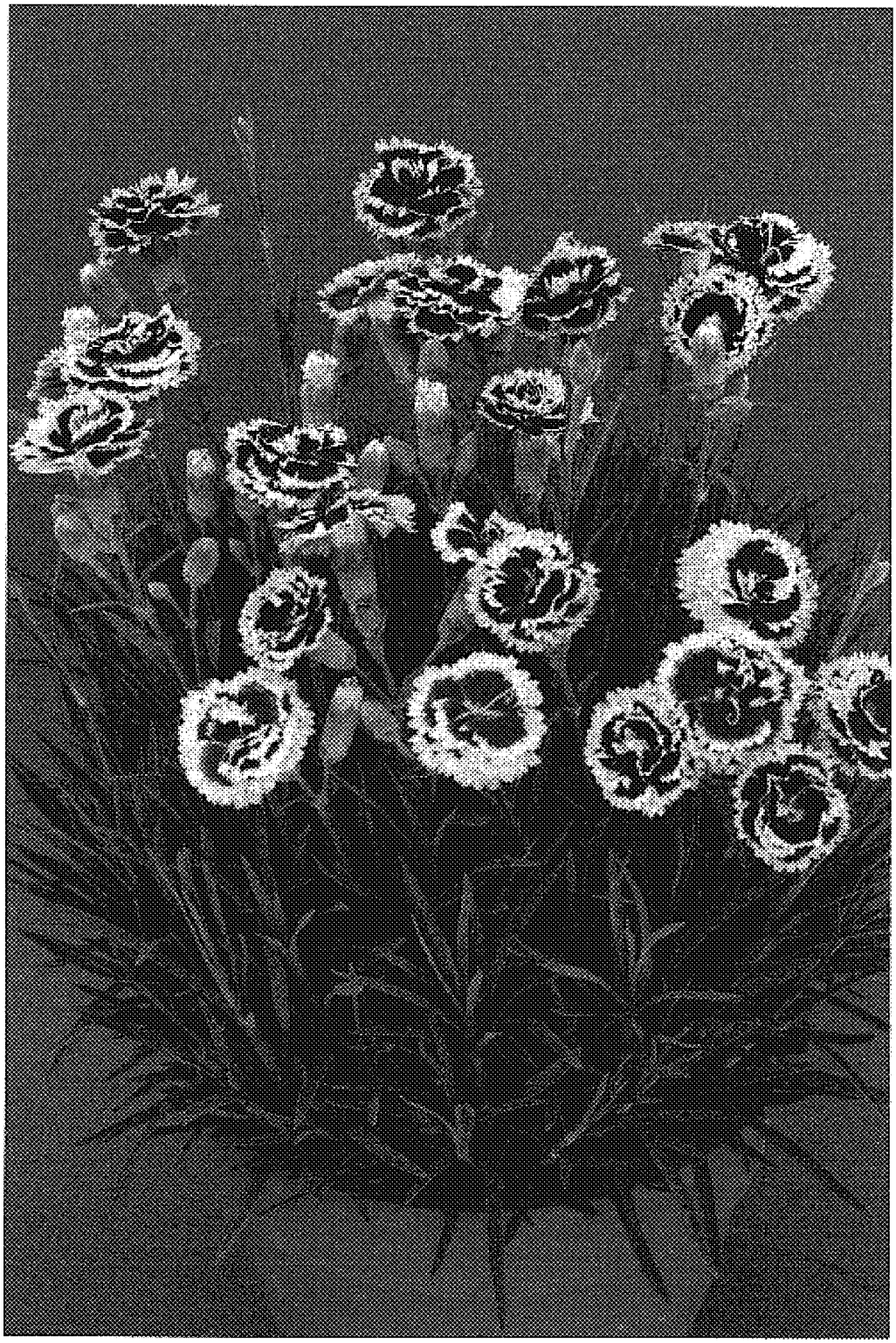
Figure 2:
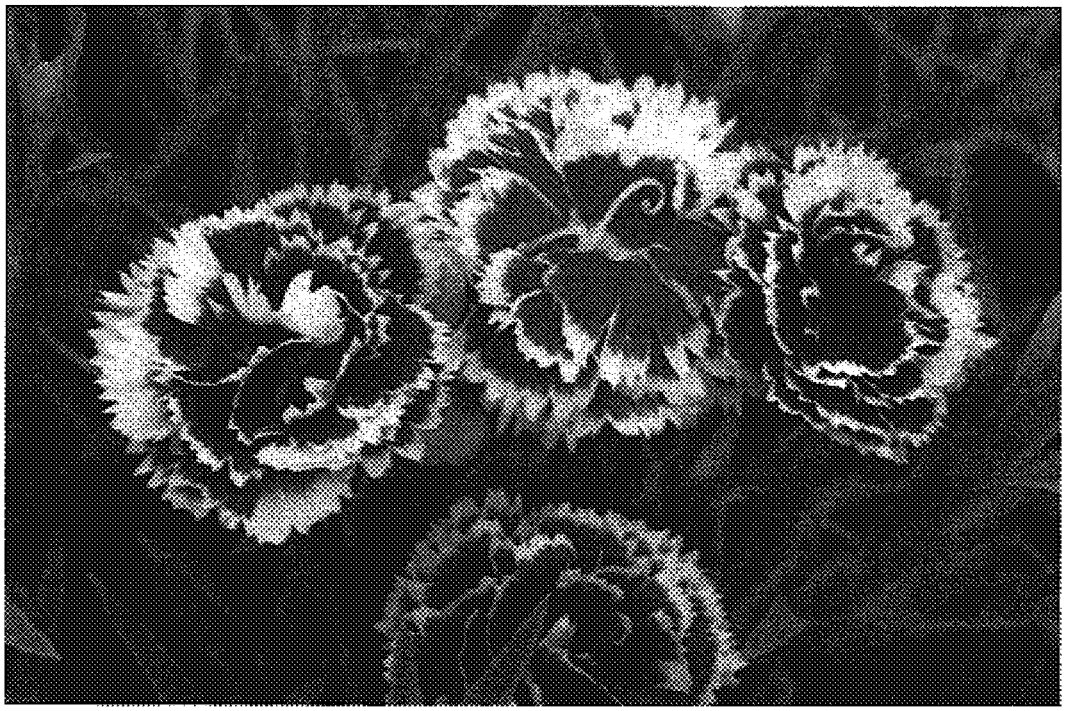

The drawing labeled as FIG. 2 is a close-up view of the flower.

All drawings were made of plants grown in 1.5-litre containers under an unheated glasshouse in Houndspool, Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'WP05 ENID'. Data was collected from plants grown in 1.5-litre containers under an unheated glasshouse in Houndspool, United Kingdom. The color determinations are in accordance with the 2001 edition of The Royal Horticultural Society Colour Chart of the Royal Horticultural Society, London, England, except where general color terms of ordinary dictionary significance are used. No chemicals were used to treat the plants. Growing conditions are typical to other *Dianthus*.

Botanical classification: *Dianthus* 'WP05 ENID'.
Species: ×*hybrida*.
Common name: Hybrid *dianthus*.
Commercial classification: Hardy perennial herb.
Use: Ornamental plant for small pots and containers.
Parentage: 'WP05 ENID' is a hybrid plant that resulted from the open pollination of a group of unidentified *Dianthus* seedlings.
- *Female parent plant.*—Unidentified individual *Dianthus* plant.
- *Male parent plant.*—Unidentified individual *Dianthus* plant.

Plant description:
- *Bloom period.*—May to October.
- *Plant habit.*—Compact mounding habit.
- *Plant height.*—20–25 cm in overall height, including flower canopy.
- *Plant width.*—25–30 cm in width.
- *Plant hardiness.*—Hardy to minus 15° Centigrade.
- *Type.*—Perennial.
- *Root system.*—Fibrous.
- *Propagation.*—Propagation is accomplished using stem cuttings.
- *Cultural requirements.*—Plant in full sun, well-drained and moderately fertile soil and keep well fertilized and watered.
- *Diseases and pests.*—Susceptible to known *Dianthus* pests and disease but no other susceptibilities to pests or disease are known to the inventor.
- *Time required to produce a rooted cutting.*—5 weeks are needed to produce a rooted cutting.
- *Temperature recommended for cuttings to produce roots.*—The air temperature needed is a minimum of 15° Centigrade air temperature and base heat of 21° Centigrade.
- *Crop time.*—3–6 months is needed to produce a finished 1.5-litre container size from a well-rooted cutting.

Foliage:
- *Stem.*—Shape: Cylindrical. Dimensions: 13 cm –20 cm in length and 3 mm in diameter. Surface: Glabrous and glaucous. Color: 145C. Branching: Numerous shoots from the axils of the lower leaves. Internode length: 10 mm–20 mm between nodes. Node dimensions: 4 mm in diameter and 3 mm in length.
- *Leaf.*—Type: Evergreen. Dimensions: 5 cm–7.5 cm in length and 3 mm in width. Color (adaxial and abaxial surfaces): 133B. Shape: Linear. Division: Simple. Apex: Acute. Base: Decurrent. Venation: Not prominent. Margins: Entire. Attachment: Sheathing. Arrangement: Opposite and spiraling up stem. Surfaces (adaxial and abaxial): Glaucous. Stipules: Present. Stipule dimensions: 2 mm. width and 8 mm. in length. Stipule color: 122A. Fragrance: Absent.

Flowers:
- *Inflorescence.*—Cymose.
- *Type.*—Salviform and symmetrical.
- *Number.*—3–7 per stem.
- *Dimensions* (*including calyx*).—30 mm in length and 35 mm in diameter.
- *Shape.*—Circular.
- *Profile.*—Reflexed.
- *Lastingness.*—10 days at 20° Centigrade on the plant.
- *Fragrance.*—Medium.
- *Flowering period.*—May–October in Devon, UK.
- *Peduncle.*—Dimensions: 20 cm–25 cm in length, 3 mm in width. Strength: Erect. Color: 133B.
- *Bud.*—Color: Each bud is 137A on apical half and 137B on basal half. Anthocyanin: Absent. Dimensions: 18–20 mm. in length and 8–9 mm. in width. Shape: Cylindrical.
- *Corolla.*—Profile: Upper part of corolla convex, lower part of corolla concave. Petal arrangement: Persistent, apopetalous, and overlapping. Margin: Crenate-dentate. Indentations: 2 mm deep. Texture: Soft. Type: Double. Number of petals: 15–20. Dimensions: 30 mm in length, 10 mm in width. Petal shape: Obdeltoid. Petal surface: Glabrous. Color pattern: Blade has a large patch of red-purple with a pale pink edge. Color of adaxial surface: Ground color of blade: Ranges between 49B and 49D. Color of band around blade: 53A. Color of middle of strap: 145C. Color of base of strap: 145D. Color of abaxial surface: Ground color of blade: 69B. Color of middle of strap: 145C. Color of base of strap: 145D.
- *Calyx.*—Dimensions: 20 mm in length and 8 mm in width. Shape: Cylindrical. Longitudinal profile: Flat. Sepals: Fused. Number of sepals: 5. Color of sepals: 143B. Anthocyanin: Absent. Splitting: Not observed.
- *Epicalyx.*—Number: 1 pair of 2 Shape: Acuminate. Dimensions: 7 mm in length and 6 mm in width. Color: 143A. Anthocyanin: Absent.
- *Bracteoles.*—Number: 2. Dimensions: 4 mm in length and 5 mm in width. Color: 143A. Anthocyanin: Absent.

Reproductive organs:
- *Stamen number.*—0–10.
- *Stamen dimensions.*—15 mm in length and 0.5 mm in width.
- *Color of filaments.*—White.
- *Anther number.*—0–10.
- *Anther dimensions.*—1 mm in length, 0.5 mm in diameter.
- *Color of anthers.*—White.

*Anther attachment.*—Dorsifixed.
*Pollen.*—Absent.
*Style number.*—2.
*Style shoulder.*—Absent.
*Color of style.*—62D.
*Style dimensions.*—25 mm in length and 0.5 mm in width.
*Stigma number.*—One.
*Stigma color.*—White.
*Stigma dimensions.*—5 mm above petals above maturity.
*Ovary position.*—Superior.
*Ovary dimensions.*—5 mm in length and 4 mm in diameter.
*Ovary shape.*—Spindle.
*Ovary color* (*upper and lower*).—145B.

Seed: 'WP05 ENID' does not set seed.

It is claimed:

1. A new and distinct cultivar of *Dianthus* plant named 'WP05 ENID' as described and illustrated herein.

* * * * *